(12) United States Patent
Shibata et al.

(10) Patent No.: US 7,470,763 B2
(45) Date of Patent: Dec. 30, 2008

(54) LATEX POLYMER PARTICLES CONTAINING FLUORESCENT SUBSTANCE OR CONTRAST MEDIUM AND PROCESS FOR PRODUCING THE SAME

(75) Inventors: Naoya Shibata, Matsudo (JP); Yukio Nagasaki, Moriya (JP); Kazunori Kataoka, Tokyo (JP)

(73) Assignee: Nanocarrier Co., Ltd., Chiba (JP)

( * ) Notice: Subject to any disclaimer, the term of this patent is extended or adjusted under 35 U.S.C. 154(b) by 383 days.

(21) Appl. No.: 10/539,746

(22) PCT Filed: Dec. 19, 2003

(86) PCT No.: PCT/JP03/16325
§ 371 (c)(1), (2), (4) Date: Jun. 20, 2005

(87) PCT Pub. No.: WO2004/056894
PCT Pub. Date: Jul. 8, 2004

(65) Prior Publication Data
US 2006/0138381 A1    Jun. 29, 2006

(30) Foreign Application Priority Data
Dec. 19, 2002   (JP)   ............ 2002-368080

(51) Int. Cl.
    *C08F 12/04*   (2006.01)
(52) U.S. Cl. ............ 526/346; 526/325; 526/319; 526/307.5
(58) Field of Classification Search ........... 526/346, 526/325, 319, 307.5
    See application file for complete search history.

(56) References Cited

U.S. PATENT DOCUMENTS

| | | | |
|---|---|---|---|
| 4,358,388 A | 11/1982 | Daniel et al. | |
| 4,735,907 A | 4/1988 | Schaeffer et al. | |
| 6,881,484 B2 * | 4/2005 | Kataoka et al. | ............ 428/407 |

FOREIGN PATENT DOCUMENTS

| | | | |
|---|---|---|---|
| EP | 1 398 635 A1 | * | 3/2004 |
| EP | 1398635 | | 3/2004 |
| EP | 1405871 | | 4/2004 |
| JP | 56-164503 | | 12/1981 |
| JP | 61-218945 | | 9/1986 |
| JP | 08-133990 | * | 5/1996 |
| JP | 10-055911 | | 2/1998 |
| WO | 97/45468 | | 12/1997 |

OTHER PUBLICATIONS

Matsuya et al., Anal. Chem., 75, 6124-6132 (2003).*
Matsuya et al., "A Core—Shell-Type Fluorescent Nanosphere Possessing Reactive Poly(ethylene glycol) Tethered Chains on the Surface for Zeptomole Detection of Protein in Time-Resolved Fluorometric Immunoassay", Anal. Chem. 2003, 75, 6124-6132.

* cited by examiner

*Primary Examiner*—Ling-Siu Choi
(74) *Attorney, Agent, or Firm*—Wenderoth, Lind & Ponack, L.L.P.

(57) ABSTRACT

This invention provides a method to effectively incorporate inorganic fluorescent substance or inorganic contrast medium into latex polymer particles which are used for diagnostic test or the like, and also provides thus produced fluorescent substance-containing latex polymer particles which show decreased non-specific adsorption of protein or the like. Said latex polymer particles are produced by making latex-forming monomer, macromer which has at least a hydrophilic polymer segment and an inorganic fluorescent substance or an inorganic contrast medium co-existent simultaneously in an aqueous medium, and subjecting them to a polymerization reaction.

9 Claims, 2 Drawing Sheets

LATEX POLYMER PARTICLES CONTAINING FLUORESCENT SUBSTANCE OR CONTRAST MEDIUM AND PROCESS FOR PRODUCING THE SAME

TECHNICAL FIELD

This invention relates to inorganic fluorescent substance- or inorganic contrast medium-containing latex polymer particles which are in particular usable for the detection of components of organisms and for diagnosis, and to a process to produce the particles. In this specification, "latex polymer particles" mean polymer particles which are capable of forming latex in aqueous medium.

BACKGROUND ART

As an example of inorganic metal-containing latex polymer particles which have conventionally been used for such purposes as the detection of components of organisms, diagnosis and the like, there can be mentioned particles which are manufactured by emulsion polymerization between an organic layer wherein hydrophobic vinyl aromatic monomer (which may optionally include comonomer) and magnetic particles are dispersed and an emulsifier-containing aqueous solution. In such emulsion polymerization, water-insoluble organic compounds are made to co-exist so that magnetic particles may efficiently be encapsulated in latex particles (e.g., Patent Document 1).

"Magnetic particles (which are synthesized in the method as mentioned in Patent Document 1) have a shape of polymer-coated magnetic body, and, therefore, the magnetic particles have different sizes depending on the particle size of magnetic body as a nucleus. Hence, it is difficult to keep the size of magnetic particles uniform, in particular when the magnetic body has a particle size in a range of 0.1 to 1.0 µm. Besides, synthetic operation is very complicated." For this reason, there has been provided another method (e.g., Patent Document 2); latex polymer particles which are a polystyrene- or styrene-butadiene copolymer are previously swollen by organic solvent and by heating, and, then, labeling material such as magnetic substance and fluorescent material is added and mixed by stirring, and, thus, said fluorescent material or the like is embedded in the vicinity of surface layer of the latex polymer particles.

The method of Patent Document 1 of emulsion polymerization for encapsulating magnetic particles in latex polymer particles has some defects. Maybe on this account, in most of other methods, swollen polymer particles are brought into contact with an aqueous solution of fluorescent substance or the like (which is to be chelated where necessary) so that the fluorescent substance or the like may thereby be mixed, or incorporated, into the polymer particles, and, in this manner, magnetic body or fluorescent substance is encapsulated or embedded in latex polymer particles (e.g., Patent Documents 3 and 4). Patent Document 3 discloses latex polymer particles which were manufactured from hydrophobic monomer such as styrene, nonionic water-soluble monomer such as acrylamide and anionic monomer such as acrylic acid, for the purpose of improving the stability of latex polymer particles in aqueous solution and of immobilizing physiologically reactive seed on said polymer particles by covalent bonding or absorption. Patent Document 4, on the other hand, uses, as a comonomer for styrene monomer or the like, a macromer which comprises poly(oxyalkylene) segment having, at one terminal, a polymerizable ethylenic group and, at the other terminal, an active ester group, with a view to providing a reactive microsphere which has excellent stability in aqueous medium, and is capable of stably immobilizing thereon functional substances such as protein by chemical bonding, and on which non-specific adsorption of protein or the like hardly occurs.

Documents which are cited above and below are identified as follows.

Patent Document 1

Japanese Patent KOKAI Publication No. Sho 56 (1981)-164503 (see page 1, right lower column, lines 2 to 14, in particular)

Patent Document 2

Japanese Patent KOKAI Publication No. Hei 10 (1998)-55911 (see page 2, right column, lines 33 to 44, and page 5, left column, lines 34 to 45, in particular)

Patent Document 3

Japanese Patent KOKAI Publication No. Sho 61 (1986)-218945 (see page 4, left lower column, lines 4 to 16, and page 3, right upper column, lines 2 to 15, in particular)

Patent Document 4

Japanese Patent KOKAI Publication No. Hei 8 (1996)-133990 (see page 2, left column [claim 1], the same page, right column, lines 18 to 28, in particular)

DISCLOSURE OF INVENTION

In Patent Document 2, as mentioned above, fluorescent material or the like is embedded in the vicinity of surface layer of latex polymer particles, simultaneously with the polymerization of bifunctional monomer or the like, and, thus, polymer of not large molecular weight, i.e., of the degree of oligomer, is adhered onto the surface layer of high-molecular material (latex polymer particles). This suggests that the embedding method of Patent Document 2 alone has a possibility that the embedded fluorescent material or the like may be released from polymer particles by washing or the like. Patent Document 4 mentions an idea of impregnating the core portion of reactive microsphere with dye or pigment for use as functional dye or the like. Patent Document 4, however, neither has any concrete mention of how to impregnate nor gives any description of reactive microsphere whose core portion was actually impregnated with dye or pigment. Patent Document 4 refers to microsphere on which non-specific adsorption of protein or the like hardly occurs. If, however, further improvement is possible, it would be desirable to provide means to that end.

Thus, the first objective of this invention is to provide a method to efficiently and stably include fluorescent substance or contrast medium in latex polymer particles (in particular such ones as mentioned in Patent Document 4, which have, on the surface layer of particles, a domain originated in macromer which gives hydrophilicity to polymer particles). Another objective of this invention is to provide latex polymer particles which stably contain fluorescent substance or contrast medium, and which show much decreased non-specific adsorption of undesirable protein or the like thereon.

The inventors of this invention have assiduously studied how to attain the above-mentioned objectives. As a result, they have found that inorganic fluorescent substance or inorganic contrast medium is efficiently and stably encapsulated or taken into polymer particles when such fluorescent substance or contrast medium is made to co-exist during the formation of latex polymer particles by the copolymerization of a latex-forming monomer and a macromer having water-soluble (or hydrophilic) polymer segment, in contrast to Patent Document 1 wherein not only magnetic particles but also water-insoluble organic compounds are made to co-exist during emulsion polymerization. The inventors have further found out that, when there are used, for the above-mentioned macromer, at least two kinds of macromers each having a poly(ethyleneglycol) segment which has at its one terminal a specific functional group, non-specific adsorption of undesirable protein or the like can significantly be decreased as compared with the case where a single kind macromer is used.

Thus, this invention provides a method to produce fluorescent substance-containing latex polymer particles, characterized in that polymerization reaction is conducted in an aqueous medium while the aqueous medium is stirred, said aqueous medium comprising:
(i) one or more kinds of latex-forming monomers,
(ii) a macromer which has, on one terminal, a polymerizable ethylenic group and has, on the other terminal, a hydrophilic polymer segment which is linked or not linked by a hydrophobic polymer segment,
(iii) a radical polymerization initiator, and
(iv) an inorganic fluorescent substance or an inorganic contrast medium.

This invention also provides, as another embodiment, hydrophobic core-hydrophilic shell type latex polymer particles which include, in their hydrophobic core domain, inorganic fluorescent substance or inorganic contrast medium, said latex polymer particles having an average particle size of 0.001 to 5 μm, and being formed by radical polymerization in an aqueous medium which comprises:
(a) 0.5 to 99.5% by weight of one or more kinds of latex-forming monomers,
(b) 0.5 to 99.5% by weight of macromer which has, on one terminal, a polymerizable ethylenic group and has, on the other terminal, a hydrophilic polymer segment which is not linked by a hydrophobic polymer segment [this macromer includes at least two kinds of macromers each of which has, on said the other terminal, a poly(ethyleneglycol) segment which carries a group selected from the group consisting of hydroxyl group, carboxyl group, aldehyde group, amino group, imino group, mercapto group, active ester-type protected hydroxyl group, active ester-type protected carboxyl group, acetal-type protected aldehyde group, organic sulfonyl-protected hydroxyl group, reactivity-protected amino group and $C_1$-$C_4$ alkoxyl group, recurring unit of said ethyleneglycol being 5 to 1200].

DESCRIPTION OF EMBODIMENTS OF INVENTION

Figure 1:
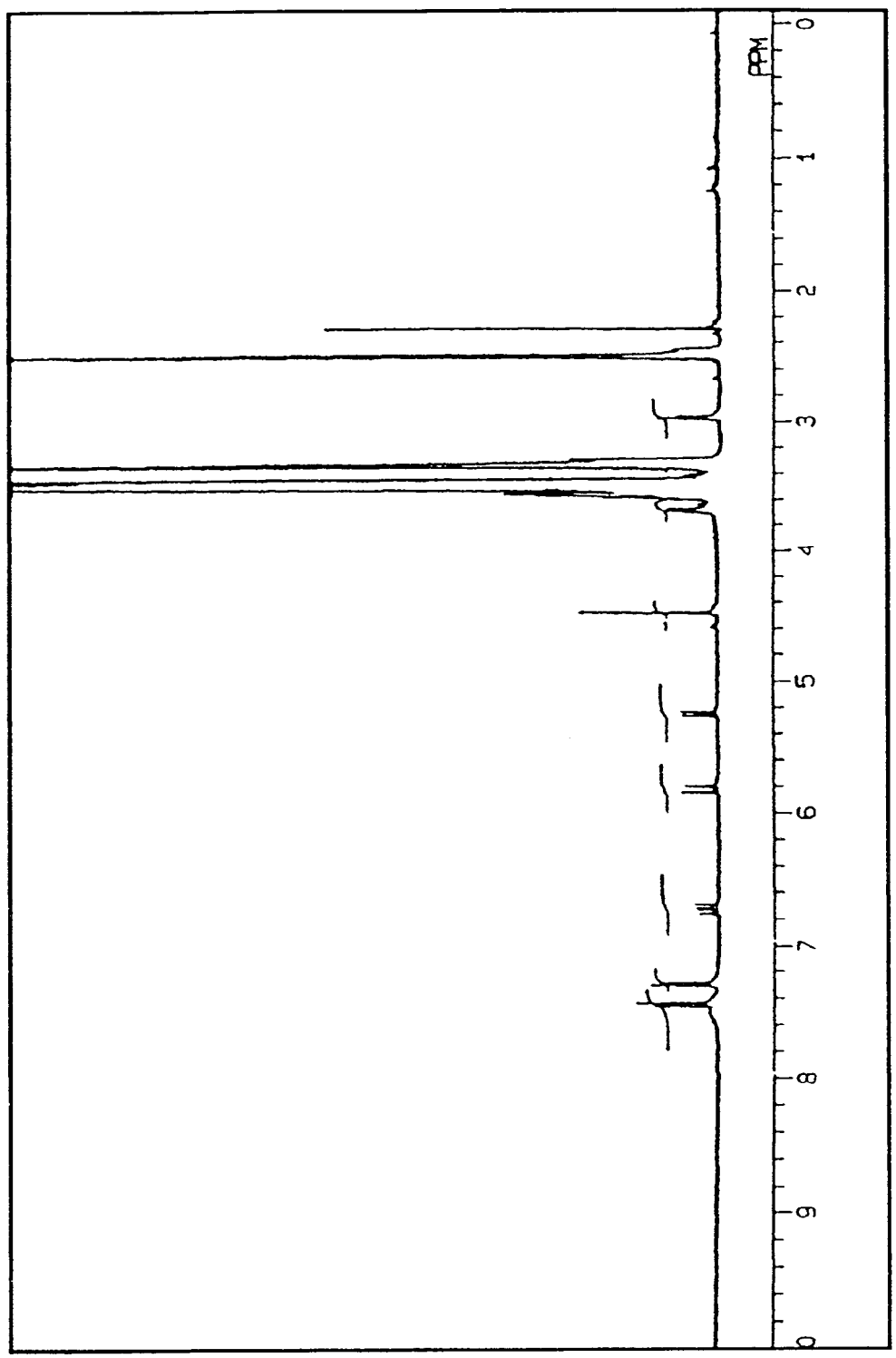
FIG. 1 is $^1$H-NMR spectrum of macromer which was obtained in Macromer Synthesis Example 1.

In this specification, "latex polymer particles" mean polymer particles which are capable of forming latex in aqueous medium. The term latex is used in a sense which is common among those skilled in the art. It means, for instance, a dispersion of polymer particles in water as a dispersing medium. The term aqueous medium means an aqueous solution which may contain water-miscible organic solvent, e.g., ethanol, methanol, tetrahydrofuran, acetone and acetonitrile, and also buffer etc. In a specific example, the aqueous medium is pure water.

"Inorganic fluorescent substance" is used in a sense which is interchangeable with fluorescent material or fluorogenic material, i.e., a material which emits remarkable luminescence with various stimulation from outside. Contrast medium means nuclear magnetic resonance imaging (MRI) agent or X-ray contrast medium. Non-restrictive, examples of inorganic fluorescent substance and inorganic contrast medium include rare-earth metals which belong to lanthanoid in periodic table of the element of the element, e.g., europium (Eu), terbium (Tb), samarium (Sm) and gadolinium (Gd), and, furthermore, certain kinds of semiconductor such as CdS, CdSe and InP. Rare-earth metals may be contained, in the form of chelate compound or chelate complex, in latex polymer particles of this invention. Fluorescent substance-containing latex particles mean polymer particles produced by copolymerization using latex-forming monomer having polymerizable ethylenic group and macromer as mentioned later, the hydrophobic core domain of which has encapsulated or taken in all or part of fluorescent substance, and from which the fluorescent substance is hardly or not released at all by usual washing or the like.

Examples of chelating agent for rare-earth metals which is advantageously usable for the formation of such particles include 1,3-diketones such as thenoyltrifluoroacetone, benzoylacetone and acetylacetone, which are not restrictive. In particular, when Gd is used as contrast medium, complexes which are sold on the market as final products under general name such as meglumine gadopentetate and gadodiamide hydrate are usable as they are. Furthermore, when rare-earth metal is to be used for fluorescent emission, Lewis base such as trioctylphosphine oxide (TOPO) and phenanthroline (Phen) may be used with rare-earth metal compound. Besides, barium, barium salt, etc., which are not rare-earth metal, are included in the above-mentioned contrast medium.

In this invention, "latex-forming monomer" includes any known monomer that is capable of forming latex by radical polymerization in aqueous medium, so long as it serves to achieve the objective of this invention. "Known" monomer means that it is publicly known in this field by literatures such as Patent Documents 1, 2 and 3 as mentioned above. Not restrictive, examples of such a monomer include hydrophobic vinyl monomer, in particular vinyl aromatic compounds such as substituted or unsubstituted styrene and 1-vinylnaphthalene, more specifically styrene, α-methylstyrene, ethylstyrene, p-bromostyrene, vinyltoluene and t-butylstyrene. Also included are $C_1$-$C_4$ alkyl (meth)acrylate, more specifically methyl acrylate, methyl methacrylate, ethyl acrylate, ethyl methacrylate, n-butyl acrylate and n-butyl methacrylate. Furthermore, substituted or unsubstituted conjugated diene, e.g., butadiene etc., is also included. Such a hydrophobic monomer is preferably used in an amount of 0.5 to 99.5% by weight, desirably 10 to 90% by weight, more desirably 20 to 80% by weight, based on the total polymer weight of latex polymer particles of this invention. Among the above-listed monomers, substituted or unsubstituted styrene is generally most suitable. When polymerizable ethylenic group of macromer which is mentioned later is aromatic monomer-originated group, also $C_1$-$C_4$ alkyl (meth)acrylate is desirably used. Examples of $C_1$-$C_4$ alkyl include methyl, ethyl, n-propyl, isopropyl, n-butyl and t-butyl. These monomers may be used in combination of two or more monomers. Incidentally, as would clearly be seen from the above-mentioned examples of (meth)acrylic esters, "(meth)acrylic acid" means acrylic acid, methacrylic acid or both.

The above-mentioned hydrophobic monomer is essential as latex-forming monomers in this invention. Said monomers may contain, as optional component, water-soluble monomer. Representative examples of water-soluble monomer are amide (meth)acrylate, 2-hydroxyethyl (meth)acrylate, 2-hydroxypropyl (meth)acrylate and N-vinylpyrrolidone, which may substitute for a part, e.g., 0 to 99%, of the above-mentioned amount of hydrophobic monomer. Furthermore, crosslinking monomer, for example a monomer corresponding to divinyl compound of the above-mentioned vinyl aromatic compound, or to biscompound of (meth)acrylic ester, specifically divinyl benzene, bis(meth)acryloylethyl, etc., may, as optional component, substitute for a part, e.g., 0 to 99%, of the above-mentioned amount of hydrophobic monomer.

This invention uses, as another essential monomer which constitutes polymer of latex polymer particles, a macromer which has at least hydrophilic polymer segment. Macromer, which is also called macromonomer, usually means a polymerizable polymer whose molecular weight is thousands to tens of thousands. In this invention, macromer also includes so-called oligomer whose molecular weight is hundreds. The macromer which is used in this invention has hydrophilic polymer (which includes oligomer; the same applies in the following) segment as an essential constituent segment. Hydrophilic segment means a segment comprising a polymer chain which becomes water-soluble as a corresponding independent polymer, not as a segment in macromer.

Such a hydrophilic segment is preferably nonionic, and, although not restrictive, comprises a main chain such as poly (ethyleneglycol) [hereinafter sometimes referred to as PEG; interchangeable with poly(oxyethylene) or poly(ethyleneoxide)], poly(vinylalcohol), poly(vinylpyrrolidone), poly(dextran), poly(dextrin), gelatin, etc. In the above-mentioned macromer, such a hydrophilic segment is connected, at one terminal, to a polymerizable ethylenic group via a suitable linking group. "Polymerizable ethylenic group" means a group which is capable of proceeding with reaction under normal radical polymerization reaction condition. Hence, not restrictive, polymerizable ethylenic group may be a group which can be present in a residue originated in monomers as listed above with respect to latex-forming monomer. Examples of such residue include (meth)acryloyl and vinylbenzyl, vinylphenyl, etc., whose aromatic ring is substituted or unsubstituted. The above-mentioned hydrophilic polymer segment, although dependent on how to prepare a corresponding macromer, is linked to the above-mentioned residue via a linking group which comprises at least one of oxygen or sulfur atom, carbonyl, carbonyloxy, oxycarbonyl, imino, carbonylimino, iminocarbonyl, $C_1$-$C_4$ alkylene and $C_1$-$C_4$ alkynylene, to make macromer or a part of macromer which is used in this invention. Such a macromer or a part thereof can be formed by known selective termination of corresponding water-soluble polymer with the above-mentioned residue; for example, in the case of synthetic polymer segment, by the terminal treatment of living polymer with (meth)acrylic acid or its reactive ester, or by living polymerization by using, as a living polymerization initiator, alcohols such as vinylbenzylalcohol; or in the case of natural water-soluble polymer segment, on the other hand, by selective treatment of one terminal of a corresponding polymer with use of (meth) acrylic acid or its reactive ester. There can be employed any of these treatments or reactions that are well known to skilled persons.

In the macromer which is used in this invention, a hydrophilic polymer segment may be linked by hydrophobic polymer segment as well as the above-mentioned linking group. In this specification, hydrophobic polymer segment means a concept opposite to the aforementioned hydrophilic polymer segment. Concretely, it is understood that an independent polymer corresponding to hydrophobic polymer segment is scarcely-soluble or insoluble in water. Not restrictive, examples of such a hydrophobic polymer segment include poly(lactide) chain, poly(ε-caprolactone) chain, poly(α- and/or β-benzyl aspartic acid) chain and poly(γ-benzyl glutamic acid) chain. Examples of polymer or macromer which has poly(ethyleneglycol) chain as a hydrophilic polymer segment, and has a chain listed above as a hydrophobic polymer segment are mentioned in U.S. Pat. No. 5,449,513 (Japanese Patent KOKAI Publication No. Hei 6-107565) and U.S. Pat. No. 5,925,720 (WO 96/33233). These segments may have a length which ranges from that of the above-mentioned oligomer to that of polymer, so long as the objective of this invention is achieved. In the case of PEG for instance, ethyleneglycol unit is preferably within a range of 5 to 1200. Anyone skilled in the art would be able to decide the chain length of any hydrophilic polymer segment other than PEG, in the light of the above-explained chain length of PEG. Hydrophobic polymer segment, on the other hand, can have a chain length of 0 to 500, or, when the polymer segment exists, 5 to 500. When such a hydrophobic polymer segment exists, it may be linked to a residue as mentioned above such as vinylbenzyl whose aromatic ring is substituted (by, for instance, $C_1$-$C_4$ alkylene, halogen atom, etc.) or unsubstituted and (meth) acryloyl via a linking group which comprises at least one of oxygen or sulfur atom, carbonyl, carbonyloxy, oxycarbonyl, imino, carbonylimino, iminocarbonyl, $C_1$-$C_4$ alkylene and $C_1$-$C_4$ alkynylene. Hydrophobic polymer segment and hydrophilic polymer segment may be linked to each other either directly or via the above-mentioned linking group.

An especially preferably macromer which is usable in this invention has no hydrophobic polymer segment, and has PEG as a hydrophilic polymer segment. This hydrophilic polymer segment serves to decrease the above-mentioned non-specific adsorption of protein or the like. Conveniently usable PEG segment carries, at an other terminal than the one which has a polymerizable ethylenic group, a reactive functional group such as hydroxyl group, aldehyde group, carboxyl group, amino group, imino group, mercapto group, active ester-type protected hydroxyl group, active ester-type protected carboxyl group, acetal-type protected aldehyde group and reactivity-protected amino group (e.g., maleimide) or the like, which, under circumstances, may form, after the deblocking of protective group, a covalent bond with a functional group which exists in biomolecule like protein, nucleic acid, sugars and composite thereof. Examples of the group at said other terminal of PEG also include $C_1$-$C_4$ alkoxyl group so as to inhibit reactivity or interaction with biomolecule, or organic sulfonyl-protected hydroxyl group which can chemically be converted into another functional group. Although not restrictive, examples of organic sulfonyl include tosyl and mesyl. The term "active ester-type protected" group means, as is well known to skilled persons, that said protected hydroxyl and carboxyl groups are each so protected as to easily form an ester with carboxyl group and amino or hydroxyl group in the above-mentioned biomolecule, respectively. An example of macromer which has an active ester-type protected hydroxyl group is given in the above-mentioned Patent Document 4. The above-mentioned WO 96/33233 refers to a macromer having hydrophobic polymer segment, and to a method to introduce multi-reactive functional group at a terminal. Thus, in accordance with these documents, any skilled person would be able to manufacture various kind of macromers which have no hydrophobic polymer segment as stated above. Representative examples of such macromer (which may contain hydrophobic polymer segment) have formula (I) as follows:

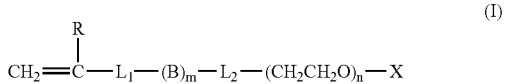

(I)

wherein R denotes hydrogen atom or $C_1$-$C_4$ alkyl group; $L_1$ denotes a linking group comprising a portion other than vinyl group of radically polymerizable monomer, e.g., methylene, substituted or unsubstituted phenylene or phenyl alkylene, oxy, carbonyl, carbonyloxy, and a combination thereof; B denotes a moiety of the following structure:

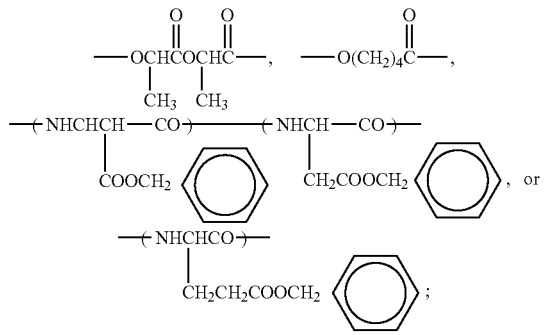

$L_2$ denotes a linking group comprising oxygen atom, $C_1$-$C_4$ alkylene, carbonyl, imino, or a combination of at least two thereof;

X denotes hydrogen atom, $C_1$-$C_4$ alkyl, $C_1$-$C_4$ alkylenecarboxyl, $C_1$-$C_4$ alkylenecarboxyl ester (said ester is exemplified by acid halide, $C_1$-$C_4$ alkyl ester and other active ester), $C_1$-$C_4$ alkyleneamino, $C_1$-$C_4$ alkylenemercapto, $C_1$-$C_4$ alkyleneacetal (e.g.:

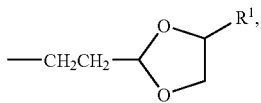

wherein $R^1$ denotes hydrogen atom or $C_1$-$C_4$ alkyl) or $C_1$-$C_4$ alkyleneoxycarbonylimidazol (e.g.:

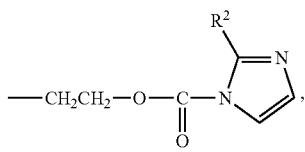

wherein $R^2$ denotes hydrogen atom or $C_1$-$C_4$ alkyl); m denotes an integer of 0 to 500, and n denotes an integer of 5 to 1200.

Especially preferable among the above-mentioned macromers is a combination of a macromer (hereinafter also referred to as non-reactive PEG macromer) wherein m denotes 0 (i.e., no hydrophobic segment is contained), and wherein X denotes hydrogen atom or $C_1$-$C_4$ alkyl (said alkyl is exemplified by such ones as have been explained with regard to (meth)acrylic ester), and at least one macromer (hereinafter also referred to as reactive PEG macromer) wherein X denotes neither hydrogen atom nor $C_1$-$C_4$ alkyl. Fluorescent substance-containing latex polymer particles which are produced from a combination of two kinds of macromers as mentioned above are not described in any prior art references, and are therefore novel so far as the inventors know. Such polymer particles which are produced from two kinds of macromers as mentioned above show unexpected effects of significant decreasing of the undesirable non-specific adsorption of protein onto the surface of particles, as compared with, for instance, functional material-immobilized microsphere as disclosed in Patent Document 4 whose recurring units comprise, as macromer, reactive PEG macromer alone. Such novel fluorescent substance- or contrast medium-containing latex polymer particles are conveniently manufactured by the method of this invention as mentioned above. In order to introduce fluorescent substance or contrast medium into core portion, one may employ another method according to which any known latex polymer particles that contain neither fluorescent substance nor contrast medium are previously prepared, and, later, fluorescent substance or contrast medium is introduced by any suitable method.

Thus, this invention provides, as another embodiment, hydrophobic core-hydrophilic shell type latex polymer particles which contain fluorescent substance in hydrophobic core domain, said latex polymer particles not limited to the production process of this invention. Incidentally, non-reactive PEG macromer and reactive PEG macromer are preferably combined so that the PEG chain length of the non-reactive PEG may be the same as, or shorter than, that of the reactive PEG. The PEG chain length of the non-reactive PEG is usually 20 to 100%, preferably 40 to 90%, of that of the reactive PEG. The molar proportion of non-reactive PEG macromer to reactive PEG macromer ranges from 1:5000 to 5000:1, preferably from 1:3000 to 3000:1, especially desirably from 1:100 to 1000:1. Latex polymer particles (which may contain fluorescent substance) having recurring units originated in two kinds of PEG macromers in the above-mentioned proportion remarkably decrease non-specific adsorption of protein or the like to the surface of the particles. Such particles are therefore especially preferably handled in vivo or in vitro with organism-originated sample. Furthermore, polymer particles prepared from two kinds of macromers improve the bonding of reactive PEG macromer-originated functional group to biomolecule. Said one or more kinds of macromers are preferably used in an amount of 0.5 to 99.5% by weight, desirably 10 to 90% by weight, more desirably 20 to 80% by weight, based on the total weight of latex polymer particles (which contain no fluorescent substance).

According to the method of this invention, the above-mentioned latex-forming monomer and the above-mentioned macromer are subjected to publicly known radical polymerization in aqueous medium. During said radical polymerization, fluorescent substance (as a chelated compound under circumstances) is made to co-exist in an amount of 0.001 to 90% by weight, preferably 0.1 to 60% by weight, especially desirably 1 to 20% by weight, based on the total weight of the above-mentioned monomer and macromer.

Radical polymerization reaction is conducted among the above-mentioned latex-forming monomer, macromer, fluorescent substance and radical polymerization initiator put in an aqueous medium, optionally with heating (up to about 100° C.). This reaction system is usually placed in inert atmosphere such as argon, nitrogen or the like. Said latex-forming monomer in an aqueous medium is conveniently chosen so that it may account for 0.1 to 50 w/w %. The above-mentioned reaction system is prepared in any order so long as polymerization reaction proceeds. Preferably, however, it should follow Examples which are mentioned later. Optimal conditions of reaction time vary depending on reaction temperature and the species of monomer. Generally, however, reaction is carried out for 24 hours. For radical polymerization initiator, any conventional initiator will do, without restriction. Representative examples of radical polymerization initiator include azo compounds such as 2,2'-azobisisobutyronitrile (AIBN), 2,2'-azobis[2-(2-imidazolin-2-yl)propane], 2,2'-azobis(2-methylbutyronitrile); and organic peroxides such as benzoyl peroxide, t-butyl hydroperoxide and diisopropyl peroxydicarbonate. Such initiator may account for 0.001 to 10 mole %, preferably 1 to 5 mole %, based on the total monomer (including macromonomer).

Thus produced latex polymer particles may be purified by centrifugal separation, sedimentation, dialysis, ultrafiltration or gel filtration, either separately or in combination. Among thus obtained latex polymer particles, those which have reactive PEG macromer-originated unit can have antibody, antigen, haptene, lectin or sugar immobilized thereon via covalent bond through any known reaction, after protective group (e.g., acetal) is deblocked where necessary. Hence, especially when two kinds of macromers are used in vivo as a targeting label or in vitro, non-specific adsorption of protein or the like hardly or not occurs at all, and, therefore, the particles are usable as an assaying system with low background.

In the following, this invention is specifically explained by working examples, which do not restrict the scope of this invention.

<Measurement Apparatus and Conditions etc.>

(1) Measurement of molecular weight:

Gel permeation chromatography (GPC) HLC-8020 made by Tosoh Corporation, Detector: Refractive Index Detector RID-6A, Column: TSK-gel (super HZ-2500, super HZ-3000, super HZ-4000), Mobile phase: 2% triethylamine-containing THF, Flow rate: 1 mL/min.

(2) Nuclear Magnetic Resonance Spectrum ($^1$H-NMR)

JEOL EX-400 (400 MHz) made by Japan Electron Optics Laboratory Co., Ltd., Solvent: DMSO-$d_6$, Measurement temperature: 20° C.

(3) Measurement of particle size:

Dynamic Light Scattering (DLS) Photometer (DLS-7000) made by Otsuka Electronics Co., Ltd.

Light Source: Ar laser (4) Measurement of intensity of fluorescence:

Spectrofluorophtometer F-2500 made by Hitachi, Ltd. Each of the obtained particle suspension was diluted to 1/500 with super high-purity water, and was subjected to measurement of intensity of fluorescence under the following measurement conditions, and, thus, intensity of fluorescence per gram of particle was calculated (based on Comparative Example 1 below as a standard). Photomultiplier voltage: 700 V, Excitation wave length: 340 nm, Fluorescence wave length: wave length which shows maximum intensity (615 to 616.5 nm)

MACROMER SYNTHESIS EXAMPLE 1

Synthesis of VB-PEG-NH$_2$

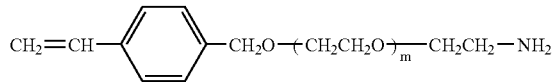

(Compound 1)

Process to Prepare Acetone-Potassium:

A reactor was fed with 35.2 mL of tetrahydrofuran (THF), 5 mL (15 mmol) of 3M potassium hydride (KH)/THF solution, 0.735 mL (10 mmol) of acetone in argon atmosphere at room temperature. The resultant mixture was stirred for 15 minutes to give 0.25 M acetone-potassium/THF solution.

Process to Synthesize VB-PEG-NH$_2$

A reactor was fed with 1 mL (2 mmol) of 2M vinylbenzylalcohol (VBA)/THF solution and 8 mL (2 mmol) of 0.25 M acetone-potassium/THF solution in argon atmosphere at room temperature. The resultant mixture was stirred for 15 minutes to give a solution of potassium alkoxide of VBA. From this reaction mixture, acetone was evaporated by vacuum drying. Later, 60 mL of THF was added, and, moreover, 11.3 mL (0.23 mol) of ethyleneoxide was added by cooled syringe. The resultant mixture was stirred for two days at room temperature to cause ring-opening polymerization, and, thus, VB-PEG-OH was synthesized.

To this ring-opening polymerization reaction product, 1.3 mL (9.4 mmol) of triethylamine was added. The resultant solution is hereinafter referred to as solution A. There was added 0.5 mL (6.5 mmol) of methanesulfonyl chloride to 10 mL of THF. The resultant solution is hereinafter referred to as solution B. Solution A was added dropwise to solution B over a period of about one hour. After the dropwise addition was over, the resultant mixture was stirred for further two hours. Then, this reaction mixture solution was filtrated. Filtrate was poured to ether to precipitate monomer. The macromer was separated by filtration, and solvent was evaporated by vacuum drying, and, thus, VB-PEG-methanesulfonyl (VB-PEG-Ms) was obtained.

In 110 mL of distilled water, 9.0 g of VB-PEG-Ms (2.34 mmol) was dissolved. The resultant solution is hereinafter referred to as solution C. Solution C was added dropwise to 500 mL of 25% ammonia water over a period of about one hour at room temperature. After the dropwise addition was over, the resultant mixture was stirred for three days at room temperature. From this reaction solution, ammonia was evaporated by evaporator, and, furthermore, the solution was concentrated to about 100 mL. This concentrated solution was poured to isopropyl alcohol which had been cooled to −15° C., and, thus, monomer was precipitated. Macromer was recovered by centrifugal separation (6000 r.p.m, 40 minutes, −10° C.). Thus obtained macromer was dissolved in benzene. After the resultant solution was freeze-dried, macromer (Compound 1, also referred to as VB-PEG-NH$_2$) was recovered.

The obtained compound was confirmed by gel permeation chromatography (GPC) (with HLC-8020 made by Tosoh Corporation) and nuclear magnetic resonance measurement apparatus (JEOL EX-400 (400 MHz) made by Japan Electron Optics Laboratory Co., Ltd.) under the above-mentioned measurement condition. From the result of GPC, it was known that PEG chain had a molecular weight of 3590, and a molecular weight distribution Mw/Mn of 1.04.

FIG. 1 shows $^1$H-NMR spectrum of VB-PEG-NH$_2$. From the $^1$H-NMR spectrum, vinyl group-introducing rate and amino group-introducing rate were calculated, and, thus, it was confirmed that vinyl group and amino group had been almost quantitatively introduced.

MACROMER SYNTHESIS EXAMPLE 2

Synthesis 2 of VB-PEG-NH$_2$

Macromer (corresponding to Compound 1) was synthesized with use of potassium hydride (KH)/THF solution in place of acetone-potassium THF solution of the above Synthesis Example 1.

Preparation of KH/THF Solution:

A vessel was fed with KH/oil in an argon atmosphere, and, then, oil content was removed with hexane. This operation was repeated three times, and, then, vacuum drying was conducted overnight to completely remove hexane. THF was added, and, thus, 3M KH/THF solution was prepared.

Process to Synthesize VB-PEG-NH$_2$

A reactor was fed with 58 mL of THF, 1 mL (2 mmol) of 2M VBA/THF solution and 0.8 mL (2.4 mmol) of 3 M KH/THF solution in argon atmosphere at room temperature. The resultant mixture was stirred for 30 minutes at room temperature to give a solution of potassium alkoxide of VBA. This solution was left to stand still for two hours to precipitate excessive KH, and, then, supernatant solution was put in a vessel in argon atmosphere. Then, 11.3 mL (0.23 mol) of ethyleneoxide was added by using cooled syringe. The resultant mixture was stirred for two days at room temperature to cause ring-opening polymerization, and, thus, VB-PEG-OH was synthesized.

To this ring-opening polymerization reaction product, 1.3 mL (9.4 mmol) of triethylamine was added. The resultant solution is hereinafter referred to as solution A. There was added 0.5 mL (6.5 mmol) of methanesulfonyl chloride to 10 mL of THF. The resultant solution is hereinafter referred to as solution B. Solution A was added dropwise to solution B over a period of about one hour. After the dropwise addition was over, the resultant mixture was stirred for further two hours. Then, this reaction mixture solution was filtrated. Filtrate was poured to ether to precipitate macromer. The macromer was separated by filtration, and solvent was evaporated by vacuum drying, and, thus, VB-PEG-Ms was obtained.

In 110 mL of distilled water, 7.7 g of VB-PEG-Ms (1.4 mmol) was dissolved. The resultant solution is hereinafter referred to as solution C. Solution C was added dropwise to 500 mL of 25% ammonia water over a period of about one hour at room temperature. After the dropwise addition was over, the resultant mixture was stirred for three days at room temperature. From this reaction solution, ammonia was evaporated by evaporator, and, then, the solution was concentrated to about 100 mL. This concentrated solution was poured to isopropyl alcohol which had been cooled to −15° C., and, thus, macromer was precipitated. Monomer was recovered by centrifugal separation (6000 r.p.m, 40 minutes, −10° C.). Thus obtained macromer was later dissolved in benzene. After the resultant solution was freeze-dried, macromer was recovered as desired.

The obtained compound was confirmed by gel permeation chromatography (GPC) (with HLC-8020 made by Tosoh Corporation) and nuclear magnetic resonance measurement apparatus (JEOL EX-400 (400 MHz) made by Japan Electron Optics Laboratory Co., Ltd.) under the above-mentioned measurement condition. From the result of GPC, it was known that PEG chain had a molecular weight of 5460, and a molecular weight distribution Mw/Mn of 1.03.

From the $^1$H-NMR spectrum, vinyl group-introducing rate and amino group-introducing rate were calculated, and, thus, it was confirmed that vinyl group and amino group had been almost quantitatively introduced.

MACROMER SYNTHESIS EXAMPLE 3

Synthesis of VB-PEG-OH

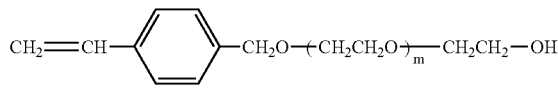

(Compound 2)

A reactor was fed with 1 mL (2 mmol) of 2M VBA/THF solution and 8 mL (2 mmol) of 0.25 M acetone-potassium/THF solution in argon atmosphere at room temperature. The resultant mixture was stirred for 15 minutes to give a solution of potassium alkoxide of VBA. From this reaction mixture, acetone was evaporated by vacuum drying. Later, 60 mL of THF was added, and, moreover, 6.8 mL (0.14 mol) of ethyleneoxide was added by using cooled syringe. The resultant mixture was stirred for two days at room temperature to cause ring-opening polymerization. Then, 3 mL of methanol was added to stop reaction. This reaction mixture solution was poured to isopropyl alcohol which had been cooled to −15° C., and, thus, macromer was precipitated. Macromer (Compound 2) was recovered by centrifugal separation (6000 r.p.m, 40 minutes, −10° C.). Solvent was removed by freeze drying.

Figure 2:
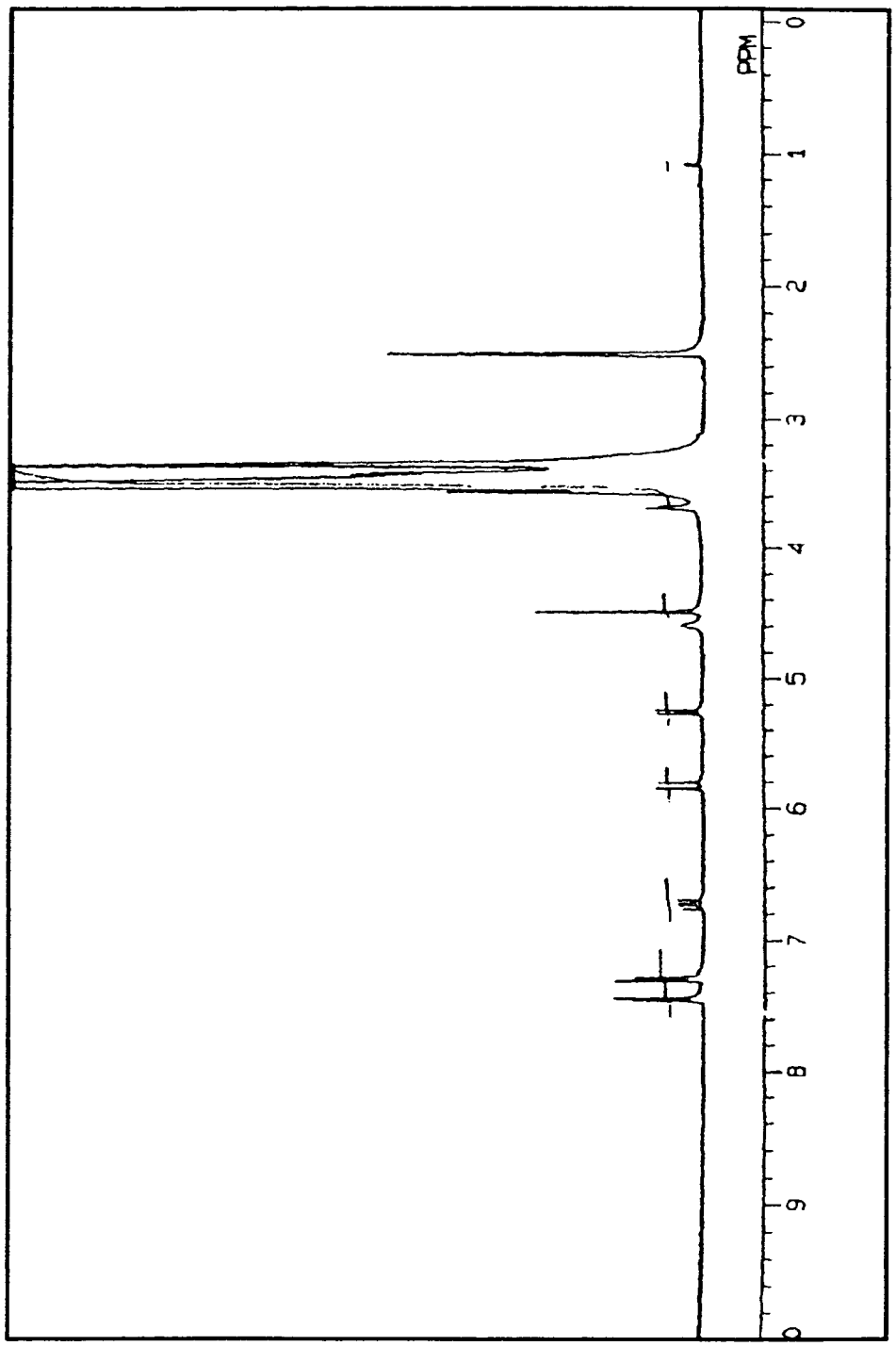
FIG. 2 is $^1$H-NMR spectrum of macromer which was obtained in Macromer Synthesis Example 2.

The obtained compound (hereinafter referred to as Compound 2 or VB-PEG-OH) was confirmed by gel permeation chromatography (GPC) (with HLC-8020 made by Tosoh Corporation) and nuclear magnetic resonance measurement apparatus (JEOL EX-400 (400 MHz) made by Japan Electron Optics Laboratory Co., Ltd.) under the above-mentioned measurement condition. FIG. 2 shows $^1$H-NMR spectrum of VB-PEG-OH. From the result of GPC, it was known that PEG chain had a molecular weight of 2850, and a molecular weight distribution Mw/Mn of 1.04.

From the $^1$H-NMR spectrum, vinyl group-introducing rate was calculated, and, thus, it was confirmed that vinyl group had been almost quantitatively introduced.

MACROMER SYNTHESIS EXAMPLE 4

Synthesis of Acetal-PEG/PLA-Methacryloyl

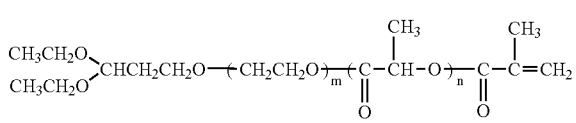

(Compound 3)

Process to Prepare Potassium-Naphthalene/THF Solution:

To a reactor which contained naphthalene in argon atmosphere, THF was added and dissolved. Then, under ice cooling, pillar-shaped potassium was added in a molar amount of 1.05 times as much as naphthalene, and the resultant mixture was stirred for one day. The resultant solution was titrated with hydrochloric acid to give 0.3263 M potassium-naphthalene/THF solution.

Synthesis of Acetal-PEG/PLA-Methacryloyl

A reactor was fed with 40 mL of THF and 0.32 mL (2 mmol) of 3,3'-diethoxy-1-propanol in argon atmosphere at room temperature. Then, 6.2 mL (2 mmol) of 0.3263 M potassium-naphthalene/THF solution was added, and the resultant mixture was stirred for 15 minutes to give a solution of potassium alkoxide solution. To this solution, 11.3 mL (0.23 mmol) of ethyleneoxide was added by cooled syringe. The resultant mixture was stirred for two days at room temperature to cause ring-opening polymerization, and, thus, acetal-PEG-OH was synthesized. To this polymerization solution, 8.4 mL (8.4 mmol) of 1 mol/L DL-lactide/THF solution was added, and stirred for three hours at room temperature for further polymerization reaction to occur. Subsequently, 4.5 mL (28 mmol) of methacrylic anhydride was added, and, after stirring for two days at room temperature, reaction was stopped. This macromer mixture solution was poured to isopropyl alcohol which had been cooled to −15° C., and, thus, macromer was precipitated. Macromer was recovered by centrifugal separation (6000 r.p.m, 40 minutes, −10° C.). Macromer was further poured to isopropyl alcohol to precipitate. Then, macromer was purified by centrifugal separation (6000 r.p.m, 40 minutes, −10° C.), and, subsequently, macromer was dissolved in benzene. By freeze-drying, macromer (Compound 3, also referred to as acetal-PEG/PLA-methacryloyl) was recovered.

The obtained compound was confirmed by gel permeation chromatography (GPC) (with HLC-8020 made by Tosoh Corporation) and nuclear magnetic resonance measurement apparatus (JEOL EX-400 (400 MHz) made by Japan Electron Optics Laboratory Co., Ltd.) under the above-mentioned measurement condition. From the result of GPC, it was known that PEG chain had a molecular weight of 5530, and a molecular weight distribution Mw/Mn of 1.03. The molecular weight of lactide chain (PLA) of acetal-PEG/PLA-methacryloyl was found to be 150, as calculated from the molecular weight of PEG chain and $^1$H-NMR spectrum which were the results of GPC. From the $^1$H-NMR spectrum, vinyl group-introducing rate was calculated, and, thus, it was confirmed that vinyl group had been almost quantitatively introduced.

EXAMPLE 1

Preparation of Fluorescent Substance-Encapsurated Amino-Terminated Core-Shell Type Latex A vessel was fed with 0.4577 g (0.5 mmol) of europium (III) thenoyl trifluoroacetone (Eu-TTA), 0.3945 g (1 mmol) of trioctylphosphine oxide (TOPO) and 20 mg (0.12 mmol) of azobisisobutyronitrile (AIBN) in argon atmosphere. Then, 20 mL of methanol was added, and the resultant mixture was dissolved by ultrasonic irradiation. Furthermore, 0.5 mL (4.35 mmol) of styrene monomer was added. The resultant solution is hereinafter referred to as chelate monomer solution. In argon atmosphere, a vessel was fed with 0.25 g (0.0487 mmol) of VB-PEG-NH$_2$ as obtained in Macromer Synthesis Example 1 and 20 mL of argon-deaerated super high-purity water. To the resultant mixture, the above-mentioned chelate monomer solution was added with stirring by three-one-motor (500 r.p.m.). After further stirring at room temperature for 30 minutes, polymerization reaction was made to occur by stirring at 60° C. for 24 hours. The resultant particle suspension was dialyzed, and purified by centrifugal separation (6000 r.p.m, 30 minutes, 4° C.). Further purification was conducted by ultracentrifugal separation (80000 r.p.m, 20 minutes, 4° C.), and, finally, the suspension was subjected to filter treatment with 0.45 μm hydrophilic membrane filter to give core-shell type latex aqueous suspension wherein amino group was bonded to surface, and wherein fluorescent substance was encapsulated in core portion.

Table-1 shows the result of calculation of fluorescent substance addition rate on the basis of the weight of particles used for the reaction, and of relative ratio of the addition rate (based on Comparative Example 1 as mentioned later). The weight of total monomer used for the reaction of Examples of this invention corresponds to the weight of particles in Comparative Examples, for calculation.

Thus obtained core-shell type latex was measured for average particle size and particle size distribution with the above-mentioned Dynamic Light Scattering (DLS) Photometer (DLS-7000) made by Otsuka Electronics Co., Ltd., and for intensity of fluorescence with Spectrofluorophtometer F-2500 made by Hitachi, Ltd. Table-2 shows the ratio of intensity of fluorescence per gram of particle (based on Comparative Example 1 as mentioned later) as well as average particle size and particle size distribution.

EXAMPLE 2

A vessel was fed with 0.4 g (0.0779 mmol) of VB-PEG-NH$_2$ as obtained in Macromer Synthesis Example 1, 0.4577 g (0.5 mmol) of europium (III) thenoyl trifluoroacetone (Eu-TTA), 0.3945 g (1 mmol) of trioctylphosphine oxide (TOPO) and 20 mg (0.12 mol) of azobisisobutyronitrile (AIBN) in argon atmosphere. Then, 20 mL of methanol was added, and the resultant mixture was dissolved by ultrasonic irradiation. Furthermore, 0.5 mL (4.35 mmol) of styrene monomer was added. To the resultant mixture, 20 mL of argon-deaerated super high-purity water was added with stirring by three-one-motor (500 r.p.m.). After stirring at room temperature for 30 minutes, polymerization reaction was made to occur by stirring at 60° C. for 24 hours. The resultant particle suspension was dialyzed, and purified by centrifugal separation (6000 r.p.m, 30 minutes, 4° C.). Finally, the suspension was subjected to filter treatment with 0.45 μm hydrophilic membrane filter to give core-shell type latex aqueous suspension wherein amino group was bonded to surface, and wherein fluorescent substance was encapsulated in core portion. Obtained data are shown in Table-1 and Table-2 below, as in Example 1.

EXAMPLE 3

A vessel was fed with 0.12 g (0.0234 mmol) of VB-PEG-NH$_2$ as obtained in Macromer Synthesis Example 1, 0.28 g (0.0893 mmol) of VB-PEG-OH as obtained in Macromer Synthesis Example 3, 0.4577 g (0.5 mmol) of europium (III) thenoyl trifluoroacetone (Eu-TTA), 0.3945 g (1 mmol) of trioctylphosphine oxide (TOPO) and 20 mg (0.12 mol) of azobisisobutyronitrile (AIBN) in argon atmosphere. Then, 20 mL of methanol was added, and the resultant mixture was dissolved by ultrasonic irradiation. Furthermore, 0.5 mL (4.35 mmol) of styrene monomer was added. To the resultant mixture, 20 mL of argon-deaerated super high-purity water was added with stirring by three-one-motor (500 r.p.m.). After stirring at room temperature for 30 minutes, polymerization reaction was made to occur by stirring at 60° C. for 24 hours. The resultant particle suspension was dialyzed, and purified by centrifugal separation (6000 r.p.m, 30 minutes, 4° C.). Finally, the suspension was subjected to filter treatment with 0.45 μm hydrophilic membrane filter to give core-shell type latex aqueous suspension wherein amino group was bonded to surface, and wherein fluorescent substance was encapsulated in core portion. Obtained data are shown in Table-1 and Table-2 below, as in Example 1.

EXAMPLE 4

A vessel was fed with 0.04 g (0.00779 mmol) of VB-PEG-NH$_2$ as obtained in Macromer Synthesis Example 1, 0.36 g (0.115 mmol) of VB—PEG-OH as obtained in Macromer Synthesis Example 3, 0.4577 g (0.5 mmol) of europium (III) thenoyl trifluoroacetone (Eu-TTA), 0.3945 g (1 mmol) of trioctylphosphine oxide (TOPO) and 20 mg (0.12 mol) of azobisisobutyronitrile (AIBN) in argon atmosphere. Then, 20 mL of methanol was added, and the resultant mixture was dissolved by ultrasonic irradiation. Furthermore, 0.5 mL (4.35 mmol) of styrene monomer was added. To the resultant mixture, 20 mL of argon-deaerated super high-purity water was added with stirring by three-one-motor (500 r.p.m.). After stirring at room temperature for 30 minutes, polymerization reaction was made to occur by stirring at 60° C. for 24 hours. The resultant particle suspension was dialyzed, and purified by centrifugal separation (6000 r.p.m, 30 minutes, 4° C.). Finally, the suspension was subjected to filter treatment with 0.45 μm hydrophilic membrane filter to give core-shell type latex aqueous suspension wherein amino group was bonded to surface, and wherein fluorescent substance was encapsulated in core portion. Obtained data are shown in Table-1 and Table-2 below, as in Example 1.

EXAMPLE 5

A vessel was fed with 0.012 g (0.00234 mmol) of VB-PEG-NH$_2$ as obtained in Macromer Synthesis Example 1, 0.388 g (0.124 mmol) of VB-PEG-OH as obtained in Macromer Synthesis Example 3, 0.4577 g (0.5 mmol) of europium (III) thenoyl trifluoroacetone (Eu-TTA), 0.3945 g (1 mmol) of trioctylphosphine oxide (TOPO) and 20 mg (0.12 mol) of azobisisobutyronitrile (AIBN) in argon atmosphere. Then, 20 mL of methanol was added, and the resultant mixture was dissolved by ultrasonic irradiation. Furthermore, 0.5 mL (4.35 mmol) of styrene monomer was added. To the resultant mixture, 20 mL of argon-deaerated super high-purity water was added with stirring by three-one-motor (500 r.p.m.). After stirring at room temperature for 30 minutes, polymerization reaction was made to occur by stirring at 60° C. for 24 hours. The resultant particle suspension was dialyzed, and purified by centrifugal separation (6000 r.p.m, 30 minutes, 4° C.). Finally, the suspension was subjected to filter treatment with 0.45 μm hydrophilic membrane filter to give core-shell type latex aqueous suspension wherein amino group was bonded to surface, and wherein fluorescent substance was encapsulated in core portion. Obtained data are shown in Table-1 and Table-2 below, as in Example 1.

REFERENTIAL EXAMPLE 1

Preparation of Core-Shell Type Latex
Aldehyde-Terminated Core-Shell Type Latex

A vessel was fed with 29.6 mg (0.18 mmol) of azobisisobutyronitrile (AIBN) in argon atmosphere. Then, 2 mL (17 mmol) of styrene solution was added. The resultant solution is hereinafter referred to as styrene solution. Another vessel was fed with 160 mL of high-purity water and 3.436 g (0.625 mmol) of acetal-PEG/PLA-methacryloyl as obtained in Macromer Synthesis Example 4, and, then, the air in vessel was replaced with argon. The resultant solution is hereinafter referred to as monomer solution. While this solution was stirred by three-one-motor (400 r.p.m.), the above-mentioned styrene solution was added. The resultant mixture was stirred at room temperature for 30 minutes, and then at 60° C. for 18 hours, and, furthermore, at 80° C. for 6 hours, and, thus, polymerization reaction was made to occur. The resultant particle suspension was filtrated by filter paper to give core-shell type latex aqueous suspension wherein acetal group was bonded to surface.

The core-shell type latex aqueous suspension was adjusted to pH 2.0 with 1M hydrochloric acid, and was then stirred for two hours. Subsequently, the solution was adjusted to pH 5.0 with 1M aqueous solution of sodium hydroxide. Then, acetal group as protective group was deblocked to give core-shell type latex aqueous suspension whose surface was now aldehyde group.

This aqueous suspension was dialyzed, and filtrated with filter paper, and was then desalted.

Thus obtained aldehyde-terminated core-shell type latex was measured for average particle size and particle size distribution with the above-mentioned Dynamic Light Scattering (DLS) Photometer (DLS-7000) made by Otsuka Electronics Co., Ltd. Particle size was 65 nm, and particle size distribution was 0.151.

REFERENTIAL EXAMPLE 2

Aldehyde-Terminated Core-Shell Type Latex

A vessel was fed with 388.2 mg (2.4 mmol) of azobisisobutyronitrile (AIBN) in argon atmosphere. Then, 27 mL (235 mmol) of styrene solution was added. The resultant solution is hereinafter referred to as styrene solution. Another vessel was fed with 400 mL of high-purity water and 8.59 g (1.56 mmol) of acetal-PEG/PLA-methacryloyl as obtained in Macromer Synthesis Example 4, and, then, the air in vessel was replaced with argon. The resultant solution is hereinafter referred to as macromer solution. While this solution was stirred by three-one-motor (400 r.p.m.), the above-mentioned styrene monomer solution was added. The resultant mixture was stirred at room temperature for 30 minutes, and then at 60° C. for 18 hours, and, furthermore, at 80° C. for 6 hours, and, thus, polymerization reaction was made to occur. The resultant particle suspension was filtrated by filter paper to give core-shell type latex aqueous suspension wherein acetal group was bonded to surface.

The core-shell type latex aqueous suspension was adjusted to pH 2.0 with 1M hydrochloric acid, and was then stirred for two hours. Subsequently, the solution was adjusted to pH 5.0 with 1M aqueous solution of sodium hydroxide. Then, acetal group as protective group was deblocked to give core-shell type latex aqueous suspension whose surface was now aldehyde group.

This aqueous suspension was dialyzed, and filtrated with filter paper, and was then desalted.

Thus obtained aldehyde-terminated core-shell type latex was measured for average particle size and particle size distribution with the above-mentioned Dynamic Light Scattering (DLS) Photometer (DLS-7000) made by Otsuka Electronics Co., Ltd. Particle size was 102.3 nm, and particle size distribution was 0.0665.

REFERENTIAL EXAMPLE 3

Amino-Terminated Core-Shell Type Latex

A vessel was fed with 20 mg (0.12 mmol) of azobisisobutyronitrile (AIBN) in argon atmosphere. Then, 0.5 mL (4.35 mmol) of styrene solution was added. The resultant solution is hereinafter referred to as styrene monomer solution. Another vessel was fed with 0.25 g (0.0487 mmol) of VB-PEG-NH$_2$ as obtained in Macromer Synthesis Example 1 in argon atmosphere, and then with 20 mL of argon-deaerated super high-purity water. While this solution was stirred by three-one-motor (500 r.p.m.), the above-mentioned styrene monomer solution was added. The resultant mixture was stirred at room temperature for 30 minutes, and then at 60° C. for 20 hours (400 r.p.m.), and, furthermore, at 80° C. for four hours, and, thus, polymerization reaction was made to occur. The resultant particle aqueous suspension was filtrated by filter paper to give core-shell type latex aqueous suspension wherein amino group was bonded to surface.

Thus obtained aldehyde-terminated core-shell type latex was measured for average particle size and particle size distribution with the above-mentioned Dynamic Light Scattering (DLS) Photometer (DLS-7000) made by Otsuka Electronics Co., Ltd. Particle size was 98.2 nm, and particle size distribution was 0.087.

COMPARATIVE EXAMPLE

Preparation of Fluorescent Substance-Encapsurated Core-Shell Type Latex by Swelling Action in Organic Solvent Comparative Example 1

To 1 mL (22 mg/mL, 0.06 mmol) of europium chloride hexahydrate, there was added 1 mL (37 mg/mL, 0.17 mmol) of acetone solution of thenoyltrifluoroacetone (TTA), and, subsequently, 2 mL (87 mg/mL, 0.23 mmol) of acetone solution of trioctylphosphine oxide (TOPO) was added, and, thus, europium chelate solution was prepared.

To 5 ml (18.13 mg/mL) of suspension of aldehyde-terminated core-shell type latex of Referential Example 1, there was added 5 mL of acetone. Furthermore, with stirring, 0.12 mL of the above-mentioned europium chelate solution (0.0018 mmol as europium chelate) was added, and the resultant mixture was stirred at room temperature under light shielding for 25 minutes. After stirring was over, acetone was evaporated with evaporator. Then, excessive europium chelate was removed by treatment with 0.2 μm hydrophilic membrane filter, and, thus, aldehyde-terminated fluorescent substance-encapsulated core-shell type latex was obtained.

Table-1 shows the result of calculation of fluorescent substance addition rate on the basis of the weight of particles used for the reaction, and of relative ratio of the addition rate (based on this Example). In this Comparative Example, the weight of particles used for reaction corresponds to the weight of total monomer used for reaction in Examples, for calculation.

Thus obtained core-shell type latex was measured for average particle size and particle size distribution with the above-mentioned Dynamic Light Scattering (DLS) Photometer (DLS-7000) made by Otsuka Electronics Co., Ltd., and for intensity of fluorescence with Spectrofluorophtometer F-2500 made by Hitachi, Ltd. Table-2 shows the ratio of intensity of fluorescence per gram of particle (based on this Example).

Comparative Example 2

To 549.2 mg (0.60 mmol) of europium (III) thenoyl trifluoroacetone (Eu-TTA) and 473.4 mg (1.2 mmol) of trioctylphosphine oxide (TOPO), there was added 4 mL of acetone, and, thus, europium chelate solution was prepared.

To 10 mL (10.0 mg/mL, distilled water) of suspension of aldehyde-terminated core-shell type latex of Referential Example 2, there was added 10 mL of acetone. Furthermore, with stirring, 0.24 mL of the above-mentioned europium chelate solution (0.036 mmol as europium chelate) was added, and the resultant mixture was stirred at room temperature under light shielding for 30 minutes. After stirring was over, acetone was evaporated with evaporator, and, then, the amount of the mixture was adjusted to 10 mL with super high-purity water by a measuring pipet. The resultant aqueous solution was subjected to centrifugal separation (3000 r.p.m, 30 minutes, 4° C.). Then, excessive europium chelate was removed by treatment with 0.2 μm hydrophilic membrane filter, and, thus, aldehyde-terminated fluorescent substance-encapsulated core-shell type latex was obtained. Data are shown in Table-1 and Table-2 below as in Example 1.

Comparative Example 3

To 32.96 mg (0.036 mmol) of europium (III) thenoyl trifluoroacetone (Eu-TTA) and 28.4 mg (0.072 mmol) of trioctylphosphine oxide (TOPO), there was added 10 mL of acetone, and, thus, europium chelate solution was prepared.

To this solution, 10 mL (10.0 mg/mL) of suspension of aldehyde-terminated core-shell type latex of Referential Example 2 was added with stirring. The resultant mixture was stirred at room temperature under light shielding for 30 minutes. After stirring was over, acetone was evaporated with evaporator, and, then, the amount of the mixture was adjusted to 10 mL with distilled water by a measuring pipet. The resultant aqueous solution was subjected to centrifugal separation (3000 r.p.m, 30 minutes, 4° C.). Then, excessive europium chelate was removed by treatment with 0.2 μm hydrophilic membrane filter, and, thus, aldehyde-terminated fluorescent substance-encapsulated core-shell type latex was obtained. Data are shown in Table-1 and Table-2 below as in Example 1.

Comparative Example 4

To 329.5 mg (0.36 mmol) of europium (III) thenoyl trifluoroacetone (Eu-TTA) and 284.1 mg (0.72 mmol) of trioctylphosphine oxide (TOPO), there was added 10 mL of acetone, and, thus, europium chelate solution was prepared.

To this solution, 10 mL (10.0 mg/mL) of suspension of aldehyde-terminated core-shell type latex of Referential Example 2 was added with stirring. The resultant mixture was stirred at room temperature under light shielding for 30 minutes. After stirring was over, acetone was evaporated with evaporator, and, then, the amount of the mixture was adjusted to 10 mL with distilled water by a measuring pipet. The resultant aqueous solution was subjected to centrifugal separation (6000 r.p.m, 30 minutes, 4° C.). Then, excessive europium chelate was removed by treatment with 0.2 μm hydrophilic membrane filter, and, thus, aldehyde-terminated fluorescent substance-encapsulated core-shell type latex was obtained. Data are shown in Table-1 and Table-2 below as in Example 1.

Comparative Example 5

To 164.8 mg (0.18 mmol) of europium (III) thenoyl trifluoroacetone (Eu-TTA) and 142.1 mg (0.36 mmol) of trioctylphosphine oxide (TOPO), there was added 5 mL of acetone, and, thus, europium chelate solution was prepared.

To this solution, 5 mL (10.0 mg/mL) of suspension of amino-terminated core-shell type latex of Referential Example 3 was added with stirring. The resultant mixture was stirred at room temperature under light shielding for 30 minutes. After stirring was over, acetone was evaporated with evaporator, and, then, the amount of the mixture was adjusted to 15 mL with distilled water by a measuring pipet. The resultant aqueous solution was subjected to centrifugal separation (6000 r.p.m, 30 minutes, 4° C.). Then, excessive europium chelate was removed by treatment with 0.45 μm hydrophilic membrane filter, and, thus, aldehyde-terminated fluorescent substance-encapsulated core-shell type latex was obtained. Data are shown in Table-1 and Table-2 below as in Example 1.

EXAMPLE 6

Preparation of Fluorescent Substance-Encapsulated Aldehyde-Terminated Core-Shell Type Latex A vessel was fed with 0.2288 g (0.25 mmol) of europium (III) thenoyl trifluoroacetone (Eu-TTA), 0.1933 g (0.49 mmol) of trioctylphosphine oxide (TOPO) and 49.3 mg (0.30 mmol) of azobisisobutyronitrile (AIBN) in argon atmosphere. Then, 10 mL of acetone and 1 mL (8.70 mmol) of styrene solution were added. The resultant solution is hereinafter referred to as styrene solution. Another vessel was fed with 80 mL of super high-purity water and 1.72 g (0.31 mmol) of acetal-PEG/PLA-methacryloyl as obtained in Macromer Synthesis Example 4, and, then, the air in vessel was replaced with argon. The resultant solution is hereinafter referred to as monomer solution. While this solution was stirred by three-one-motor (400 r.p.m.), the above-mentioned styrene monomer solution was added. The resultant mixture was stirred at room temperature for 30 minutes, and then at 60° C. for 24 hours (400 r.p.m.), and, thus, polymerization reaction was made to occur. After polymerization was over, acetone was evaporated by evaporator. The resultant particle suspension was purified by centrifugal separation (2500 r.p.m, 30 minutes, 4° C.). Finally, the suspension was subjected to filter treatment with 0.2 μm hydrophilic membrane filter to give acetal-terminated fluorescent substance-encapsulated core-shell type latex.

Then, the core-shell type latex solution was adjusted to pH 2.0 with 1M hydrochloric acid, and was then stirred for two hours. Subsequently, the solution was adjusted to pH 5.0 with 1M aqueous solution of sodium hydroxide. Then, acetal group as protective group was deblocked to give core-shell type latex aqueous suspension whose surface was now aldehyde group.

This aqueous suspension was dialyzed, and filtrated with filter paper, and was then desalted. Data are shown in Table-1 and Table-2 below as in Example 1.

EXAMPLE 7

Preparation of Fluorescent Substance-Encapsulated Acetal-Terminated Core-Shell Type Latex A vessel was fed with 0.0572 g (0.062 mmol) of europium (III) thenoyl trifluoroacetone (Eu-TTA), 0.0483 g (0.12 mmol) of trioctylphosphine oxide (TOPO) and 20 mg (0.12 mmol) of azobisisobutyronitrile (AIBN) in argon atmosphere. Then, 5 mL of acetone and 1.3 mL (11.3 mmol) of styrene solution were added. The resultant solution is hereinafter referred to as styrene solution. Another vessel was fed with 20 mL of super high-purity water and 0.43 g (0.078 mmol) of acetal-PEG/PLA-methacryloyl as obtained in Macromer Synthesis Example 4, and, then, the air in vessel was replaced with argon. The resultant solution is hereinafter referred to as monomer solution. While this solution was stirred by three-one-motor (400 r.p.m.), the above-mentioned styrene monomer solution was added. The resultant mixture was stirred at room temperature for 30 minutes, and then at 60° C. for 24 hours (400 r.p.m.), and, thus, polymerization reaction was made to occur. After polymerization was over, acetone was evaporated by evaporator. The resultant particle suspension was purified by centrifugal separation (10000 r.p.m, 30 minutes, 4° C.). Finally, the suspension was subjected to filter treatment with 0.2 μm hydrophilic membrane filter to give acetal-terminated fluorescent substance-encapsulated core-shell type latex. Data are shown in Table-1 and Table-2 below as in Example 1.

EXAMPLE 8

A vessel was fed with 0.5721 g (0.62 mmol) of europium (III) thenoyl trifluoroacetone (Eu-TTA), 0.4833 g (1.23 mmol) of trioctylphosphine oxide (TOPO) and 20 mg (0.12 mmol) of azobisisobutyronitrile (AIBN) in argon atmosphere. Then, 5 mL of acetone and 1.3 mL (11.3 mmol) of styrene solution were added. The resultant solution is hereinafter referred to as styrene solution. Another vessel was fed with 20 mL of super high-purity water and 0.43 g (0.078 mmol) of acetal-PEG/PLA-methacryloyl as obtained in Macromer Synthesis Example 4, and, then, the air in vessel was replaced with argon. The resultant solution is hereinafter referred to as monomer solution. While this solution was stirred by three-one-motor (400 r.p.m.), the above-mentioned styrene monomer solution was added. The resultant mixture was stirred at room temperature for 30 minutes, and then at 60° C. for 24 hours (400 r.p.m.), and, thus, polymerization reaction was made to occur. After polymerization was over, acetone was evaporated by evaporator. The resultant particle suspension was purified by centrifugal separation (10000 r.p.m, 30 minutes, 4° C.). Finally, the suspension was subjected to filter treatment with 0.2 μm hydrophilic membrane filter to give acetal-terminated fluorescent substance-encapsulated core-shell type latex. Data are shown in Table-1 and Table-2 below as in Example 1.

EXAMPLE 9

A vessel was fed with 1.1441 g (1.25 mmol) of europium (III) thenoyl trifluoroacetone (Eu-TTA), 0.9666 g (2.45 mmol) of trioctylphosphine oxide (TOPO) and 20 mg (0.12 mmol) of azobisisobutyronitrile (AIBN) in argon atmosphere. Then, 5 mL of acetone and 1.3 mL (11.3 mmol) of styrene solution were added. The resultant solution is hereinafter referred to as styrene solution. Another vessel was fed with 20 mL of super high-purity water and 0.43 g (0.078 mmol) of acetal-PEG/PLA-methacryloyl as obtained in Macromer Synthesis Example 4, and, then, the air in vessel was replaced with argon. The resultant solution is hereinafter referred to as monomer solution. While this solution was stirred by three-one-motor (400 r.p.m.), the above-mentioned styrene monomer solution was added. The resultant mixture was stirred at room temperature for 30 minutes, and then at 60° C. for 24 hours (400 r.p.m.), and, thus, polymerization reaction was made to occur. After polymerization was over, acetone was evaporated by evaporator. The resultant particle suspension was purified by centrifugal separation (10000 r.p.m, 30 minutes, 4° C.). Finally, the suspension was subjected to filter treatment with 0.2 μm hydrophilic membrane filter to give acetal-terminated fluorescent substance-encapsulated core-shell type latex. Data are shown in Table-1 and Table-2 below as in Example 1.

TABLE 1

Fluorescent substance addition rate, and relative ratio of the amount of fluorescent substance added

| No. | How to introduce fluorescent substance | Surface functional group | Amount of fluorescent substance added (nmol) | Weight of monomer added (g) *1 | Weight of particles (g) *2 | Fluorescent substance addition rate (mmol/g) *3 | Fluorescent substance addition rate (mmol/g) *4 | Relative ratio of the amount of fluorescent substance added *5 |
|---|---|---|---|---|---|---|---|---|
| Ex. 1 | Method of this invention | Amino group | 0.5 | 0.703 | | 0.711 | | 36 |
| Ex. 2 | Method of this invention | Amino group | 0.5 | 0.853 | | 0.586 | | 30 |
| Ex. 3 | Method of this invention | Amino group | 0.5 | 0.853 | | 0.586 | | 30 |
| Ex. 4 | Method of this invention | Amino group | 0.5 | 0.853 | | 0.586 | | 30 |
| Ex. 5 | Method of this invention | Amino group | 0.5 | 0.853 | | 0.586 | | 30 |
| CEx. 2 | Swelling action by organic solvent | Aldehyde group | 0.018 | | 0.1 | | 0.180 | 9 |
| CEx. 3 | Swelling action by organic solvent | Aldehyde group | 0.036 | | 0.1 | | 0.360 | 18 |
| CEx. 4 | Swelling action by organic solvent | Aldehyde group | 0.36 | | 0.1 | | 3.600 | 181 |
| CEx. 5 | Swelling action by organic solvent | Amino group | 0.18 | | 0.05 | | 3.600 | 181 |
| CEx. 1 | Swelling action by organic solvent | Aldehyde group | 0.0018 | | 0.09 | | 0.020 | 1 |
| Ex. 6 | Method of this invention | Aldehyde group | 0.25 | 2.626 | | 0.095 | | 5 |
| Ex. 7 | Method of this invention | Acetal group | 0.062 | 1.608 | | 0.039 | | 2 |
| Ex. 8 | Method of this invention | Acetal group | 0.62 | 1.608 | | 0.386 | | 19 |
| Ex. 9 | Method of this invention | Acetal group | 1.25 | 1.608 | | 0.777 | | 39 |

Ex.: Example
CEx.: Comparative Example
*1: Total weight of particle-constituting main component (macromer + styrene) added (corresponding to the weight of particles used for the reaction of Comparative Examples 1 to 5)
*2: Weight of particles used for the reaction
*3: Molar amount of fluorescent substance added per gram of particle-constituting main component (macromer + styrene) used for the reaction
*4: Molar amount of fluorescent substance added per gram of particles used for the reaction
*5: Relative ratio of the amount of fluorescent substance added as compared with Comparative Example 1

TABLE 2

Average particle size and the ratio of intensity of fluorescence

| No. | How to introduce fluorescent substance | Surface functional group | Relative ratio of the amount of fluorescent substance added *1 | Average particle size (nm) | Particle size distribution | Excitation wave length (nm) | Wave length of fluorescence (nm) | Ratio of intensity of fluorescence *2 |
|---|---|---|---|---|---|---|---|---|
| Ex. 1 | Method of this invention | Amino group | 36 | 162.7 | 0.056 | 340 | 616 | 8.1 |
| Ex. 2 | Method of this invention | Amino group | 30 | 163.2 | 0.037 | 340 | 616.5 | 8.3 |

TABLE 2-continued

Average particle size and the ratio of intensity of fluorescence

| No. | How to introduce fluorescent substance | Surface functional group | Relative ratio of the amount of fluorescent substance added *1 | Average particle size (nm) | Particle size distribution | Excitation wave length (nm) | Wave length of fluorescence (nm) | Ratio of intensity of fluorescence *2 |
|---|---|---|---|---|---|---|---|---|
| Ex. 3 | Method of this invention | Amino group | 30 | 160.9 | 0.115 | 340 | 616 | 10.6 |
| Ex. 4 | Method of this invention | Amino group | 30 | 147.3 | 0.094 | 340 | 616 | 9.6 |
| Ex. 5 | Method of this invention | Amino group | 30 | 150.9 | 0.088 | 340 | 616.5 | 10.1 |
| CEx. 2 | Swelling action by organic solvent | Aldehyde group | 9 | 106.7 | 0.043 | 340 | 616.5 | 1.6 |
| CEx. 3 | Swelling action by organic solvent | Aldehyde group | 18 | 107.9 | 0.048 | 340 | 616.5 | 6.1 |
| CEx. 4 | Swelling action by organic solvent | Aldehyde group | 181 | 123.2 | 0.089 | 340 | 616 | 7.8 |
| CEx. 5 | Swelling action by organic solvent | Amino group | 181 | 107.9 | 0.039 | 340 | 615 | 7.1 |
| CEx. 1 | Swelling action by organic solvent | Aldehyde group | 1 | 65.1 | 0.078 | 340 | 616.5 | 1.0 |
| Ex. 6 | Method of this invention | Aldehyde group | 5 | 52.7 | 0.120 | 340 | 616.5 | 0.8 |
| Ex. 7 | Method of this invention | Acetal group | 2 | 121.0 | 0.064 | 340 | 616.5 | 1.9 |
| Ex. 8 | Method of this invention | Acetal group | 19 | 118.8 | 0.041 | 340 | 616.5 | 0.6 |
| Ex. 9 | Method of this invention | Acetal group | 39 | 81.8 | 0.057 | 340 | 616.5 | 1.6 |

*1: Relative ratio of the amount of fluorescent substance added as compared with Comparative Example 1
*2: Relative ratio of the intensity of fluorescence per gram of particle as compared with Comparative Example 1

It is known from the above-mentioned data that the process of this invention to manufacture latex polymer particles provides latex polymer particles which efficiently and stably contain fluorescent substance or contrast medium.

EXAMPLE 10

Each of aqueous particle suspensions which had been obtained according to the methods of Examples 1 to 5 and Comparative Examples 1 to 5 was adjusted to a particle concentration of 2 mg/mL with super high-purity water. Another each of said aqueous particle suspensions was adjusted with super high-purity water so that the intensity of fluorescence as measured might be about 15000. Then, each of thus prepared aqueous particle suspensions which had been unified with regard to either particle concentration or the intensity of fluorescence was diluted to 1/500 with a buffer (1/15 M PBS, pH 7.4, which contained 0.05 wt % sodium dodecyl sulfate (SDS)), and was subsequently measured for the intensity of fluorescence by time-resolved fluorescence measurement under the following measuring conditions. Later, the suspensions were stored at 37° C., and were measured for the intensity of fluorescence under the same conditions after three days, five days and seven days. The intensity of fluorescence was measured three times for each measurement, and, so, an average was obtained from thus measured three values. With use of this average value, the rate of change of the intensity of fluorescence with lapse of time was calculated, based on the intensity of fluorescence immediately after the dilution with buffer as a standard (100%), and, thus, the particles were compared with respect to fluorescence stability.

<Measurement Apparatus and Conditions etc.>
Multi-detection Microplate Reader Power Scan HT made by Dainippon Pharmaceutical Co., Ltd.
Light Source: 10 W Xenon Flash Lamp, Excitation Wave Length: 340 nm, Fluorescence Wave Length: Standard Interference Filter 620/40 nm, Sensitivity: 120
Measurement Times: 50 times
Time span between transfer to the location of measurement and irradiation from light source: 500 μsec
Measurement Interval: 10 msec
Retardation Time: 200 μsec
Measurement Time: 400 μsec <Results>
Table-3 shows the intensity of fluorescence when particle concentration was adjusted to 2 mg/mL, and how the intensity of fluorescence changed with lapse of time. Initial intensity of fluorescence was clearly higher in Examples 1 to 5 than in Comparative Examples 1 to 5. With regard to how the intensity of fluorescence changed with lapse of time, 90% or more of the initial intensity was maintained at 37° C. even after seven days in Examples. In Comparative Examples, however, the intensity lowered to 62 to 85%. This result shows that the fluorescence in Examples was more stable.

Table-4 shows how the intensity of fluorescence changed with lapse of time when the initial intensity of fluorescence was unified at about 15000. Whereas, in Examples, 95% or more of the initial intensity was maintained at 37° C. after seven days, it lowered to 78 to 84% in Comparative Examples. This result shows that the particles of Examples were more stable with lapse of time than those of Comparative Examples.

TABLE 3

Evaluation of fluorescence stability (unified particle concentration: 2 mg/mL)

| Examples | Average of fluorescence intensity at time 0 | After 3 days (%) | After 5 days (%) | After 7 days (%) |
|---|---|---|---|---|
| Ex. 1 | 16625 | 92.5 ± 1.9 | 90.5 ± 2.8 | 91.6 ± 1.8 |
| Ex. 2 | 15003 | 95.0 ± 1.5 | 93.3 ± 3.3 | 94.6 ± 3.1 |
| Ex. 3 | 17746 | 98.6 ± 1.2 | 96.2 ± 3.2 | 97.2 ± 2.1 |
| Ex. 4 | 17381 | 97.9 ± 2.2 | 96.5 ± 3.0 | 96.4 ± 0.7 |
| Ex. 5 | 15873 | 98.6 ± 1.1 | 95.2 ± 3.7 | 98.2 ± 3.5 |
| CEx. 1 | 950 | 68.8 ± 2.2 | 63.7 ± 1.9 | 62.1 ± 2.8 |
| CEx. 2 | 4382 | 86.5 ± 3.4 | 77.6 ± 3.9 | 81.1 ± 3.1 |
| CEx. 3 | 9483 | 89.4 ± 3.9 | 76.8 ± 5.2 | 78.8 ± 3.0 |
| CEx. 4 | 11869 | 91.0 ± 3.6 | 82.3 ± 4.3 | 84.5 ± 3.5 |
| CEx. 5 | 14073 | 93.2 ± 2.2 | 85.6 ± 0.9 | 84.2 ± 2.9 |

TABLE 4

Evaluation of fluorescence stability (unified fluorescence intensity: about 15000 count)

| Examples | Average of fluorescence intensity at time 0 | After 3 days (%) | After 5 days (%) | After 7 days (%) |
|---|---|---|---|---|
| Ex. 1 | 16756 | 97.2 ± 2.3 | 93.8 ± 1.7 | 95.5 ± 2.7 |
| Ex. 2 | 13651 | 98.6 ± 1.4 | 95.3 ± 2.8 | 97.8 ± 2.6 |
| Ex. 3 | 12896 | 102.4 ± 0.6 | 96.9 ± 3.8 | 101.0 ± 2.5 |
| Ex. 4 | 14923 | 103.1 ± 1.2 | 98.8 ± 2.1 | 100.5 ± 2.5 |
| Ex. 5 | 15317 | 100 ± 2.5 | 97.7 ± 2.3 | 96.7 ± 3.1 |
| CEx. 1 | 15314 | 79.6 ± 0.7 | 76.1 ± 1.1 | 78.2 ± 2.8 |
| CEx. 2 | 14863 | 79.6 ± 2.4 | 82.8 ± 2.4 | 81.2 ± 3.1 |
| CEx. 3 | 12786 | 84.2 ± 2.3 | 83.4 ± 1.7 | 84.1 ± 2.7 |
| CEx. 4 | 13619 | 93.8 ± 2.3 | 77.7 ± 2.6 | 78.0 ± 3.2 |
| CEx. 5 | 13608 | 83.9 ± 1.8 | 80.5 ± 2.1 | 81.8 ± 2.1 |

INDUSTRIAL APPLICABILITY

The process of this invention provides latex polymer particles which efficiently and stably contain fluorescent substance or contrast medium. Hence, not restrictively, this invention is applicable in medical field and in the field of manufacture of diagnostic medicines.

The invention claimed is:

1. A process for producing fluorescent substance—or inorganic contrast medium—containing latex polymer particles, which comprises conducting a polymerization reaction in an aqueous medium while the aqueous medium is stirred, said aqueous medium comprising:
    (i) one or more latex-forming monomers,
    (ii) a macromer which has, on one terminal, a polymerizable ethylenic group and has, on the other terminal, a hydrophilic polymer segment which is linked or not linked by a hydrophobic polymer segment,
    (iii) a radical polymerization initiator, and
    (iv) an inorganic fluorescent substance or an inorganic contrast medium.

2. A process of claim 1 wherein hydrophilic polymer segment is originated from water-soluble polymer which is selected from the group consisting of poly(ethyleneglycol), poly(vinylalcohol), poly(vinylpyrrolidone), poly(dextran), poly(dextrin) and gelatin, and wherein hydrophobic polymer segment is originated from scarcely water-soluble polymer selected from the group consisting of poly(lactide), poly(ε-caprolactone), poly(α- and/or β-benzyl aspartic acid) and poly(γ-benzyl glutamic acid).

3. A process of claim 1 wherein macromer has no hydrophobic polymer segment, and wherein hydrophilic polymer segment is originated from poly(ethyleneglycol).

4. A process of claim 1 wherein macromer is of two or more kinds each of which has no hydrophobic polymer segment, and each of which has, at the other terminal, a poly(ethyleneglycol) segment which carries a group selected from the group consisting of hydroxyl group, carboxyl group, aldehyde group, amino group, imino group, mercapto group, active ester-type protected hydroxyl group, active ester-type protected carboxyl group, acetal-type protected aldehyde group, organic sulfonyl-protected hydroxyl group, reactivity-protected amino group and $C_1$-$C_4$ alkoxyl group.

5. A process of claim 1 wherein there are two macromers, the first macromer having no hydrophobic polymer segment, and having, at the other terminal, a poly(ethyleneglycol) segment which carries a group selected from the group consisting of hydroxyl group and $C_1$-$C_4$ alkoxyl group, the second macromer having no hydrophobic polymer segment, and having, at the other terminal, a poly(ethyleneglycol) segment which carries a group selected from the group consisting of carboxyl group, aldehyde group, amino group, imino group, mercapto group, active ester-type protected hydroxyl group, active ester-type protected carboxyl group, acetal-type protected aldehyde group, reactivity-protected amino group and organic sulfonyl-protected hydroxyl group, said segment of the first macromer having a chain length which is the same as, or shorter than, the chain length of said segment of the second macromer, and the molar proportion of the first macromer to the second macromer ranging from 1:5000 to 5000:1.

6. A process of claim 5 wherein the number of recurring unit of ethyleneglycol in the first macromer is an integer of 5 to 1200, the number of recurring unit of ethyleneglycol in the second macromer is an integer of 5 to 1200, and wherein the number of the first macromer recurring unit is the same as, or smaller than, the number of the second macromer recurring unit.

7. A process of any one of claims 1 to 5 wherein one or more kinds of latex-forming monomers are selected from the group consisting of styrene, α-methylstyrene, p-bromostyrene, vinyltoluene, 1-vinylnaphthalene, $C_1$-$C_4$ alkyl (meth)acrylate and divinyl benzene.

8. A process of claim 1 wherein inorganic fluorescent substance and inorganic contrast medium are in the form of chelate compound.

9. A process of claim 1 wherein macromer has general formula (I) as follows:

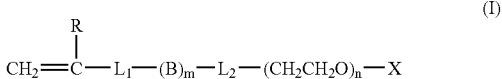

wherein R denotes hydrogen atom or $C_1$-$C_4$ alkyl group; $L_1$ denotes a linking group comprising a portion other than vinyl group of radically polymerizable monomer; B denotes a moiety of a structure selected from the following:

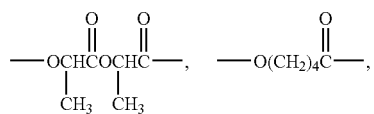

-continued

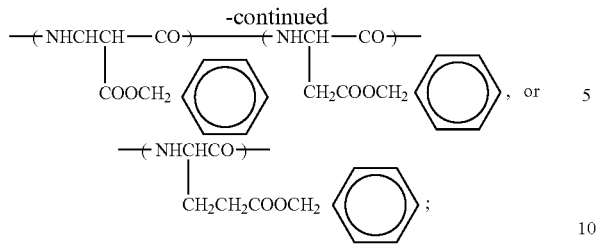, or $L_2$ denotes a linking group comprising oxygen atom, $C_1$-$C_4$ alkylene, carbonyl, imino, or a combination of at least two thereof;

X denotes hydrogen atom, $C_1$-$C_4$ alkyl, $C_1$-$C_4$ alkylenecarboxyl, $C_1$-$C_4$ alkylenecarboxyl ester, $C_1$-$C_4$ alkylenecarboxylic acid halide, $C_1$-$C_4$ alkyleneamino, $C_1$-$C_4$ alkylenemercapto, $C_1$-$C_4$ alkyleneacetal, $C_1$-$C_4$ alkyleneoxycarbonylimidazol; m denotes an integer of 0 to 500, and n denotes an integer of 5 to 1200.

* * * * *